(12) United States Patent
Zhou

(10) Patent No.: US 11,079,214 B2
(45) Date of Patent: Aug. 3, 2021

(54) SPACE DIVISION MULTIPLEXING OPTICAL COHERENCE TOMOGRAPHY USING AN INTEGRATED PHOTONIC DEVICE

(71) Applicant: Lehigh University, Bethlehem, PA (US)

(72) Inventor: Chao Zhou, Bethlehem, PA (US)

(73) Assignee: LEHIGH UNIVERSITY

( * ) Notice: Subject to any disclaimer, the term of this patent is extended or adjusted under 35 U.S.C. 154(b) by 0 days.

(21) Appl. No.: 16/612,905

(22) PCT Filed: May 14, 2018

(86) PCT No.: PCT/US2018/032529
§ 371 (c)(1),
(2) Date: Nov. 12, 2019

(87) PCT Pub. No.: WO2018/209339
PCT Pub. Date: Nov. 15, 2018

(65) Prior Publication Data
US 2020/0166328 A1    May 28, 2020

Related U.S. Application Data

(60) Provisional application No. 62/505,199, filed on May 12, 2017.

(51) Int. Cl.
*G01B 9/02* (2006.01)
*A61B 5/00* (2006.01)
(Continued)

(52) U.S. Cl.
CPC ........ *G01B 9/02051* (2013.01); *A61B 5/0066* (2013.01); *G01B 9/02004* (2013.01);
(Continued)

(58) Field of Classification Search
CPC ............ G01B 9/02051; G01B 9/02004; G01B 9/02019; G01B 9/02028; G01B 9/02091;
(Continued)

(56) References Cited

U.S. PATENT DOCUMENTS 7,242,833 B2 * 7/2007 Yang .................. A61B 1/00096
385/115
8,781,271 B1 7/2014 Karras
(Continued)

FOREIGN PATENT DOCUMENTS

EP            3431918 A1 * 1/2019 ............. G02B 6/125
WO    WO 2014194028 A1   12/2014
WO    WO 2018055606 A1    3/2018

OTHER PUBLICATIONS

Ma, Yangjin et al., "Ultralow Loss Single Layer Submicron Silicon Waveguide Crossing for Soi Optical Interconnect," Optics Express 29382, vol. 21, No. 24, Nov. 20, 2013, pp. 1-9.
(Continued)

*Primary Examiner* — Tarifur R Chowdhury
*Assistant Examiner* — Jonathon Cook
(74) *Attorney, Agent, or Firm* — The Belles Group, P.C.

(57) ABSTRACT

Integrated photonic chips and related systems and methods suitable for space-division multiplexing optical coherence tomography scanning are disclosed. In one embodiment, the photonic chip comprises a substrate, an optical input port which receives an incident sampling beam from an external light source, a plurality of optical output ports configured to transmit a plurality of sampling beams from the chip to a sample to capture scanned images of the sample, and a plurality of interconnected and branched waveguide channels formed in the substrate. Waveguide channels in a splitter region divide the sampling beam into the plurality of sampling beams at the output ports. Terminal portions of the waveguide channels in a time delay region associated with
(Continued)

each output port have different predetermined lengths to create an optical time delay between the sampling beams. In some embodiments, the chip further comprises an interferometer region to create interference patterns.

17 Claims, 8 Drawing Sheets

(51) Int. Cl.
    *G02B 6/125* (2006.01)
    *G02B 6/28* (2006.01)
    *A61B 3/10* (2006.01)
(52) U.S. Cl.
    CPC ..... *G01B 9/02019* (2013.01); *G01B 9/02028* (2013.01); *G01B 9/02091* (2013.01); *G02B 6/125* (2013.01); *G02B 6/2861* (2013.01); *A61B 3/102* (2013.01); *A61B 5/0084* (2013.01); *A61B 2562/0233* (2013.01); *G01B 2290/65* (2013.01)
(58) Field of Classification Search
    CPC ...... A61B 5/0066; A61B 3/102; G02B 6/125; G02B 6/2861
    See application file for complete search history.

(56) References Cited

U.S. PATENT DOCUMENTS

| | | | |
|---|---|---|---|
| 8,855,452 B2 | 10/2014 | Andry et al. | |
| 8,971,676 B1 | 3/2015 | Thacker et al. | |
| 9,247,624 B2 | 1/2016 | Tan et al. | |
| 9,400,169 B2 | 7/2016 | Zhou | |
| 2014/0078510 A1* | 3/2014 | Rubio Guivernau | G01B 9/02082 356/479 |
| 2014/0160488 A1* | 6/2014 | Zhou | G01B 9/02028 356/479 |
| 2014/0293290 A1 | 10/2014 | Kulkarni | |
| 2014/0328556 A1* | 11/2014 | Rubio Guivernau | A61B 5/0066 385/1 |
| 2015/0124261 A1* | 5/2015 | Jaillon | A61B 3/102 356/479 |
| 2016/0045106 A1* | 2/2016 | Jaillon | G01B 9/02027 351/221 |
| 2016/0178346 A1 | 6/2016 | Kulkarni | |
| 2016/0231101 A1 | 8/2016 | Swanson | |
| 2016/0357007 A1* | 12/2016 | Swanson | G02B 6/3548 |
| 2016/0370169 A1 | 12/2016 | Zhou | |
| 2017/0363415 A1* | 12/2017 | Frisken | G01B 9/02028 |

OTHER PUBLICATIONS

Sanchis, Pablo et al., "Highly Efficient Crossing Structure for Silicon-On-Insulator Waveguides," Optics Letters, vol. 34, No. 18, Sep. 15, 2009, pp. 1-3.

Yurtsever, Gunay, "Integrated Photonic Circuit in Silicon on Insulator for Fourier Domain Optical Coherence Tomography," Optical Coherence Tomography and Coherence Domain Optical Methods in Biomedicine XIV, (2010), pp. 1-5.

Zhang, Yi, et al., "A Compact and Low-Loss Silicon Waveguide Crossing for O-Band Optical Interconnect," Proceedings of SPIE, SPIEDigitalLibrary.org/conference-proceedings-of-spie, Mar. 8, 2014, pp. 1-9.

International Search Report and Written Opinion issued in PCT/US2018/32529, dated Jul. 31, 2018, pp. 1-11.

\* cited by examiner

SPACE DIVISION MULTIPLEXING OPTICAL COHERENCE TOMOGRAPHY USING AN INTEGRATED PHOTONIC DEVICE

CROSS-REFERENCE TO RELATED APPLICATIONS

The present application is a U.S. national stage application under 35 U.S.C. § 371 of PCT/US2018/032529 filed May 14, 2018, which claims the benefit of U.S. Provisional Patent Application Ser. No. 62/505,199 filed May 12, 2017, the entireties of which are herein by reference.

STATEMENT OF GOVERNMENT INTEREST

This invention was made with government support under National Institutes of Health (NIH R21 EY-026380, K99/R00 EB-010071) and National Science Foundation (NSF DBI-1455613, IIP-1640707, and IIP-1623823). The government has certain rights in the invention.

BACKGROUND OF THE INVENTION

The present invention generally relates to optical coherence tomography (OCT) imaging systems, and more particularly to such a system incorporating an integrated photonic chip.

Improving imaging speed is a main driving force for the development of optical coherence tomography (OCT). Space-division multiplexing optical coherence tomography (SDM-OCT) is a recently developed parallel OCT imaging method used to achieve multi-fold speed improvement. However, the assembly of multiple fiber optics components conventionally used in such systems may be labor-intensive and susceptible to errors which makes it challenging for mass-production. In addition, the numerous components of an OCT system consume space and are not readily amenable for incorporation into a compact imaging device which may be used in various medical diagnostic settings or for other uses. Improvements in SDM-OCT systems are desired.

SUMMARY OF THE INVENTION

A wide-field high-speed SDM-OCT system using an integrated photonic chip is disclosed that can be reliably manufactured with high precision and low per-unit cost facilitating the broad dissemination of the SDM-OCT technology. The present chip takes advantage of advances in the field of silicon photonics. In one embodiment, the present photonic chip replaces at least the fiber-based optical components of the traditional OCT system with on-chip photonic components to improve equipment reliability and permit creation of mass-producible compact SDM-OCT imaging devices.

The present chip-based SDM-OCT system can improve the imaging speed by a factor of 10 or more while maintaining the sensitivity in various applications, including ophthalmology, cardiovascular imaging, endoscopic imaging, cancer imaging, dental applications, research imaging applications, and others.

In one embodiment, the photonic chip may comprise on-chip combined splitter and optical time delay regions or areas formed by a plurality of interconnected branched waveguides formed in a substrate which define optical splitters. Multiple branches of waveguides and cascading rows of splitters may be provided in some configurations to successively split an incident singular sampling beam in each row into a plurality of sampling beams output from the chip. The waveguides may be channels formed by etching or deposition such as doping the substrate which create differential indices of refraction that force the light signals or waves to travel within the waveguides. In some embodiments, the substrate may be formed of solely silicon or a composite silicon on insulator (SOI).

The chip may include a single optical input port which receives a sampling light beam generated by a long coherence light source and plurality of spatially separated optical output ports for scanning multiple sampling beams simultaneously in parallel onto the surface of a sample to be scanned by the SDM-OCT system. Terminal portions of the waveguide channels associated with each output port have predetermined different lengths to create an optical time delay between each sampling beam for capturing space division multiplexed OCT scanned images of the sample. Sampling light signals reflected from the sample are returned simultaneously in parallel back through the same on-chip splitter and time delay structure following the sampling light path in reverse direction for further processing as described herein to generate digital images of the sample using one or more interferometers and additional image processing devices described herein.

In another embodiment, a low insertion loss photonic chip is disclosed herein which further includes an on-chip photonic interferometer unit, different sampling and reflected light signal paths through the chip, and a reference light input port. The various waveguide channels are configured and operable to process sampling light signals, reflected light signals, and reference light signals to create interference signals on the chip. A plurality of interference signals are emitted from the chip simultaneously in parallel which are further processed to create digital scanned images of the sample as further described herein.

In one aspect, an integrated photonic chip suitable for space-division multiplexing optical coherence tomography scanning comprises: a substrate; an optical input port configured to receive an incident singular sampling beam from an external light source; a plurality of optical output ports configured to transmit a plurality of sampling beams from the chip to a sample to capture scanned images of the sample; and a multiple branched waveguide structure optically coupling the input port to each of the output ports, the waveguide structure comprising a plurality of interconnected waveguide channels formed in the substrate; the waveguide channels configured to define a plurality of photonic splitters which divide the incident singular sampling beam received at the input port into the plurality of sampling beams at the output ports; wherein portions of the waveguide channels between the photonic splitters and output ports have different predetermined lengths to create an optical time delay between each of the plurality of sampling beams. The light source may be a wavelength-tunable long coherence light source in one embodiment. A difference in the predetermined lengths between the waveguide channels is selected to produce an optical delay shorter than a coherence length of the light source between the plurality of sampling beams so that when images are formed, signals from different physical locations are detected in different frequency bands.

In another aspect, a low loss integrated photonic chip suitable for space-division multiplexing optical coherence tomography scanning comprises: a substrate; an optical input port configured to receive an incident singular sampling beam from an external light source; a reference light input port configured to receive reference light from an external reference light source; a plurality of optical output ports configured to transmit a plurality of sampling beams from the chip to a sample to capture scanned images of the sample; a multiple branched waveguide structure optically coupling the input port to each of the output ports, the waveguide structure comprising a plurality of interconnected waveguide channels formed in the substrate, the waveguide channels defining a splitter region and an interferometer region; the waveguide channels in the splitter region configured to define a plurality of photonic splitters which divide the incident singular sampling beam received at the input port into the plurality of sampling beams at the output ports; wherein portions of the waveguide channels between the photonic splitters and output ports have different predetermined lengths to create an optical time delay between each of the plurality of sampling beams; the waveguide channels in the interferometer region configured to define a plurality of photonic interferometers, the photonic interferometers optically coupled to the waveguide channels in the time delay region and the reference light; wherein the photonic interferometers are arranged to receive a plurality of reflected light signals returned from the sample, the photonic interferometers being configured and operable to combine the reflected light signals with the reference light to produce a plurality of interference signals which are emitted from interference signal output ports of the photonic chip. The light source may be a wavelength-tunable long coherence light source in one embodiment. A difference in the predetermined lengths between the waveguide channels is selected to produce an optical delay shorter than a coherence length of the light source between the plurality of sampling beams so that when images are formed, signals from different physical locations are detected in different frequency bands.

BRIEF DESCRIPTION OF THE DRAWINGS

The features of the exemplary embodiments will be described with reference to the following drawings where like elements are labeled similarly, and in which.

All drawing shown herein are schematic and not to scale. Parts given a reference number in one figure may be considered to be the same parts where they appear in other figures without a reference number for brevity unless specifically labeled with a different part number and described herein.

DETAILED DESCRIPTION

Figure 1:
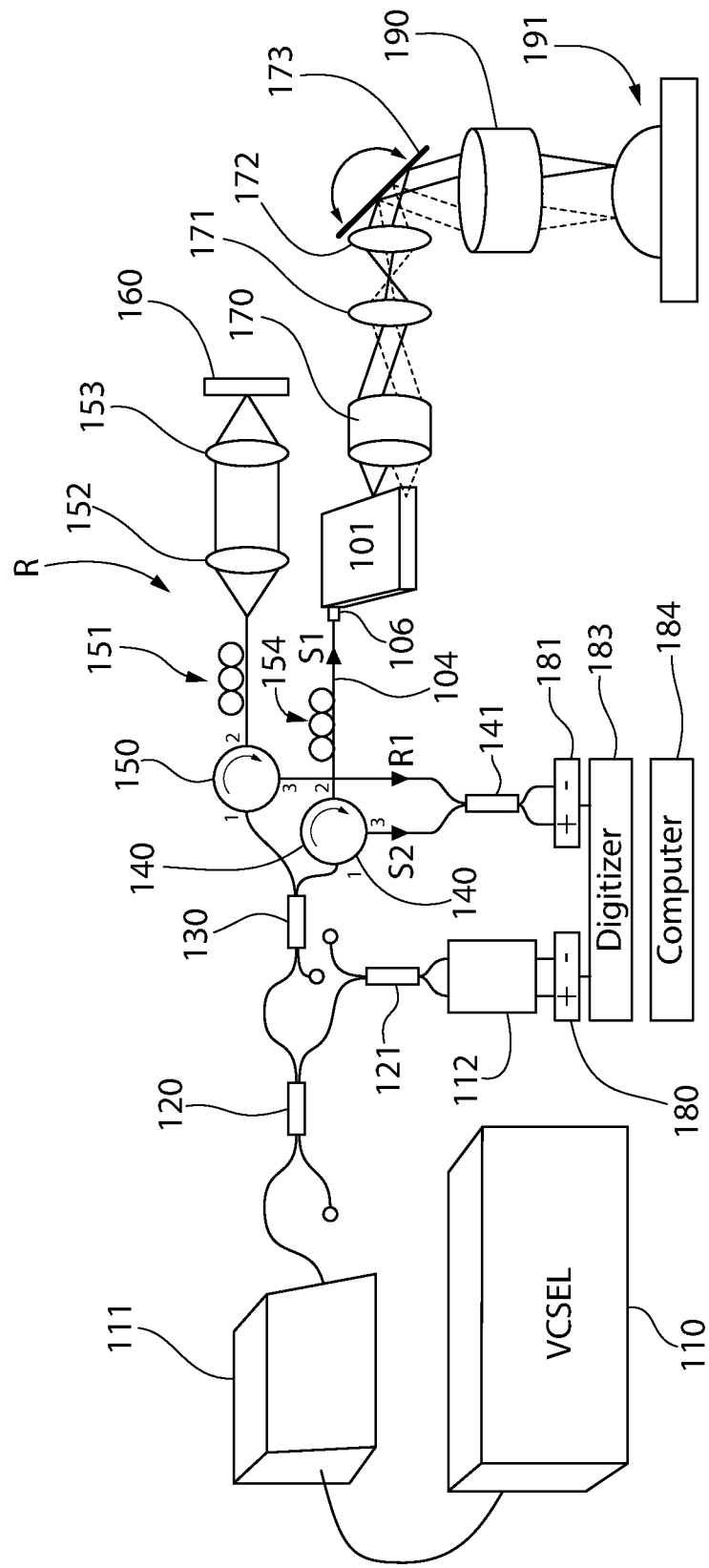
FIG. 1 is a schematic diagram of a space-division multiplexing optical coherence tomography (SDM-OCT) system incorporating a photonic chip according to one embodiment of the present disclosure.

The features and benefits of the invention are illustrated and described herein by reference to non-limiting exemplary embodiments. This description of the embodiments is intended to be read in connection with the accompanying drawings, which are to be considered part of the entire written description. Accordingly, the invention expressly should not be limited to such embodiments illustrating some possible non-limiting combination of features that may exist alone or in other combinations of features; the scope of the invention being defined by the claims appended hereto.

In the description of embodiments disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "affixed," "connected," "coupled," "interconnected," and similar refer to a relationship wherein structures may be secured or attached to one another either directly or indirectly through intervening structures, as well as both movable or rigid attachments or relationships, unless expressly described otherwise.

Recently, in commonly owned U.S. Pat. No. 9,400,169 incorporated herein by reference in its entirety, a parallel OCT imaging method, namely space-division multiplexing OCT (SDM-OCT), was disclosed which is based on a single source and detection unit. In SDM-OCT, the sample arm beam is split into multiple channels, with different optical delays in each channel in order to generate multiplexed interference signals that can be detected simultaneously. The optical delays were created in one embodiment with optical fiber-based elements comprising a planar light wave circuit splitter and an optical delay element comprising a plurality of optical fibers each having a different length to produce different optical delays in the sampling light beams transmitted to and reflected back from the sample (see, e.g. FIG. 1 in U.S. Pat. No. 9,400,169). Split beams were used to image different segments of the sample, hence the imaging speed was increased by a factor equal to the number of beams. A high imaging speed of 800,000 A-scans/s was demonstrated in this first prototype system by creating eight-beam illumination using a long-coherence-length VCSEL laser running at 100 kHz.

Although the foregoing SDM-OCT offered scalable speed improvement with a simple system configuration, the inventors discovered that the first lab prototype SDM-OCT required extensive time and manual effort to assemble the multiple custom fiber components and control optical delays for each channel, which limits the broad dissemination of the SDM-OCT technology.

SDM-OCT System With Prototype Integrated Photonic Chip

To construct SDM-OCT easily and reliably, the present disclosure eliminates the foregoing optical fiber-based delay elements which are replaced using silicon photonics. The present invention provides an SDM-OCT system 100 with an integrated photonic chip 101 comprising photonic components configured to produce optical delays in the sampling and return path light beams. Integration of such components onto a photonic chip has advantages of cost, size and stability of the system. The progress in nano/micro-fabrication of these photonic integrated circuits (PICs) has leveraged on the significant advancement in the Si-based processing capabilities, which in turn results in significant cost reduction in large scale manufacturability of such technology. The PICs also provide the ability to achieve new functionalities with increased yield and reduced errors in packaging. Integration of OCT components such as interferometer and spectrometer onto a photonic chip has been previously reported. In the case of SDM-OCT system, using a PIC chip to replace fiber-based space-division multiplexing components is potentially advantageous, since custom optical delays and spacing between each output beam can be precisely defined lithographically with sub-micron tolerances during the fabrication process.

Figure 2:
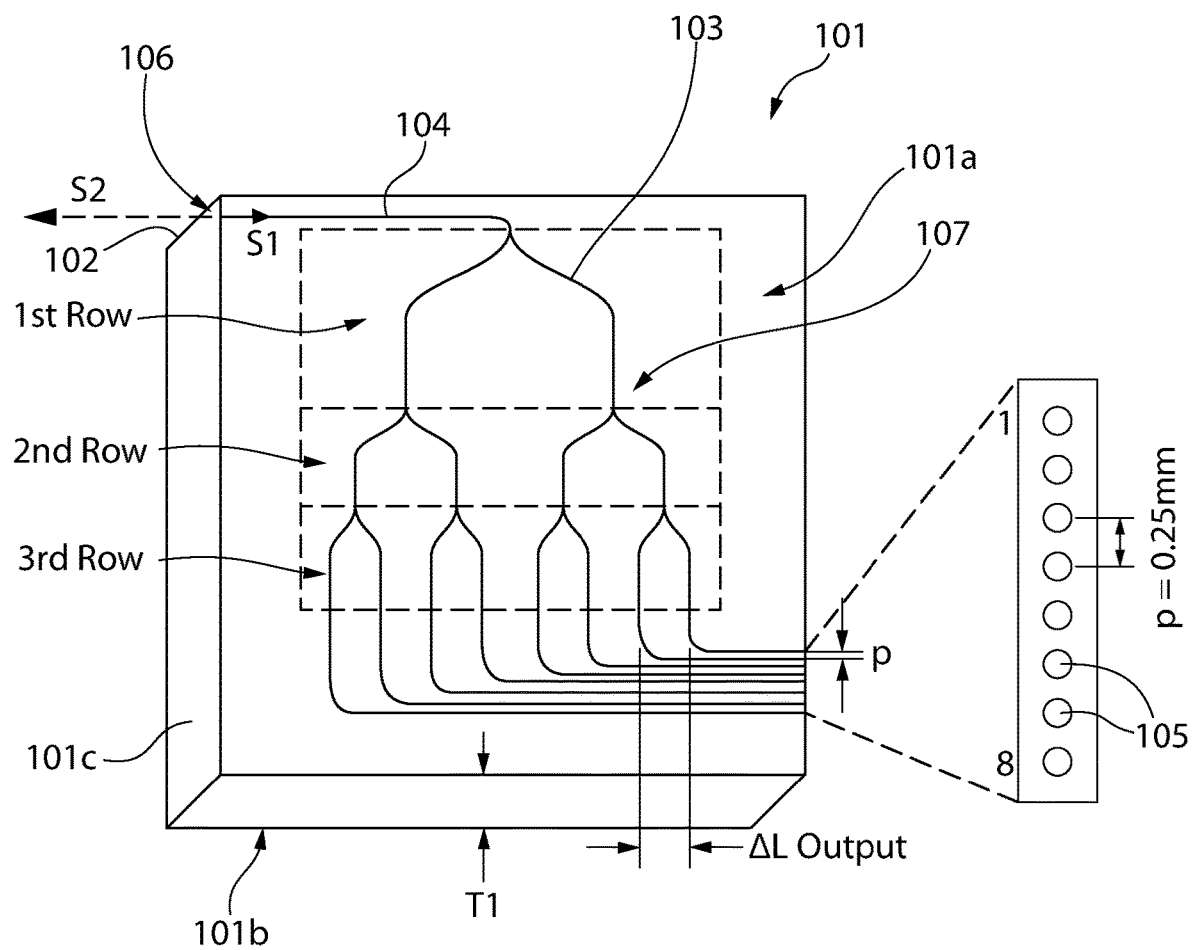
FIG. 2 is a schematic diagram of the photonic chip of FIG. 1 showing an exemplary waveguide architecture.
Figure 3:
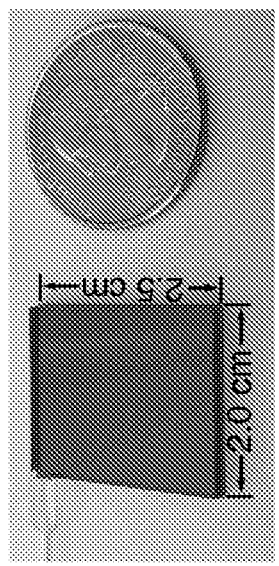
FIG. 3 is a photographic image of a prototype chip of FIG. 1 for size comparison to U.S. currency.

FIG. 1 shows a schematic diagram of a prototype photonic chip-based SDM-OCT system 100 used in the test setup to demonstrate the performance of such a system. In this prototype, traditional fiber-based components used to produce the optical delay between the sampling beam channels or paths, including a planar light wave circuit splitter and a fiber array with different optical delays, were replaced by a single integrated photonic chip 101. The schematic layout of the silicon-based photonic chip 101 is shown in FIG. 2. FIG. 3 depicts an actual photographic image of the fabricated prototype chip. Photonic chip 101 comprises a substrate 102 which may have a generally rectangular prismatic or cuboid configuration in one embodiment including two opposing parallel major surfaces 101a, 101b defining a thickness T measured therebetween and four perpendicular side surfaces 101c defining a perimeter of the chip. Substrate 102 is formed of a material having a first refractive index RI-1. In the prototype system, the substrate 102 had a thickness T1 of about 1-2 mm. Other thicknesses, however, may be used for substrate 102.

The substrate 102 of photonic chip 101 may be made of any suitable single material or multi-layered composite combination of materials conventionally used for constructing a photonic chip with waveguides, such as for example without limitation silicon or silicon-on-insulator (SOI). In one embodiment, photonic chip 101 is constructed of an SOI substrate. SOI chips typically comprise a silicon (Si) base layer, intermediate silicon dioxide ($SiO_2$) insulator layer, and thin top crystalline silicon layer typically with a thickness less than the insulator layer. The top silicon layer which guides the light beams or waves has a refractive index $n=3.45$ and the $SiO_2$ insulator layer has a refractive index $n=1.45$. Other materials besides silicon, such as Indium Phosphide (InP), Lithium Niobate ($LiNbO_3$), Silicon Nitride ($Si_3N_4$) and Gallium Arsenide (GaAs), etc., however may be used in other embodiments.

With continuing reference to FIG. 2, the photonic chip 101 is patterned with a waveguide structure having an array or plurality of interconnected branched waveguides. The waveguides may be in the form of waveguide channels 103 in the illustrated embodiment configured to create on-chip photonic beam splitter and optical time delay units or regions. Waveguide channels 103 direct and guide the incident beam on chip 101 to propagate and follow the optical light paths indicated in the figure through the chip, thereby advantageously allowing channels of different lengths to be created in the time delay region which produce an optical delay between the channels for a space division multiplexing OCT system.

The patterned waveguide channels 103 may be formed in substrate 102 by conventional semiconductor fabrication techniques or methods known in the art. An example of a suitable semiconductor method that may be used is a combination of photolithography or deep UV (ultraviolet) lithography to define the desired waveguide channel pattern followed by selectively etching the Si top layer in the case of an SOI chip 101 to form the waveguides. The comparatively large difference in the refractive indices noted above between the $SiO_2$ insulator layer ($n=1.45$) and Si top layer ($n=3.45$) noted above confines the electromagnetic field into the top Si layer causing the electromagnetic light signals or waves in the optical spectrum to travel within the confines of waveguide channels 103 in the photonic chip 101.

Another example method that may be used for forming waveguide channels 103 is doping the substrate in the manner well known and used in the fabrication of semiconductors. Doping may involve processes such as diffusion or ion implantation to introduce a dopant element to select areas of the silicon substrate to create the desired pattern of waveguide channels 103. The doped channels have a refractive index RI-2 different than the base silicon material refractive index RI-1, thereby causing the light signals or wave to follow the doped channel pattern. Other semiconductor fabrication techniques beyond those noted above used in silicon photonics however may be used in other embodiments.

In the prototype chip-based SDM-OCT system 100, the amplified incident beam from light source 110 was directly coupled and input into the chip 101 with an optical fiber 104 from the circulator 140 as shown in FIG. 1. Chip 101 includes an input port 106 formed on a first one of the side surfaces 101c which directly couples to input optical fiber 104 and a plurality of output ports 105 formed on a different second one of the side surface 101c. Of course in other embodiments, the input and output ports 106, 105 may be formed on any two different side surfaces 101c of the photonic chip 101 depending on the locations of the these ports desired for the scanning device. The sides selected for the input and output ports 106, 105 may vary and are dependent upon efficient use of chip space to minimize the size of the chip and/or to optimize the arrangement for the physical instrument or equipment in which the chip will be integrated. Accordingly, the arrangement does not limit the invention and the illustrate embodiment represents one of many possible configurations possible.

The prototype photonic chip 101 had the following design parameters: Wavelength range: 1310+/−60 nm; Coupling: match SMF-28 fiber mode (9.2 um MFD) at input and output; Output pitch p=250 um (0.25 mm); Waveguide path length difference ΔL=2.5 mm; Index contrast: 1.5%; Waveguide dimensions: 4.0 um (Width)×4.5 um (Height); and Bending radius: 2.3 mm. Other design parameters may be used for other embodiments and applications.

The photonic chip 101 comprises an on-chip splitter and time delay formed by specially configuring the multiple branched waveguide structure created using the waveguide channels 103. In the prototype, as an example without limitation, a horizontal three-row cascade of 1×2 photonic waveguide splitters 107 formed by multiple branched on-chip waveguide channels 103 were used to evenly and gradually split the incident sampling light S1 in each row from the initial singular beam or channel into final 8 beams or channels (dashed lines in FIG. 2 indicating each row of splitters on the chip). Each waveguide splitter 107 is formed by a branch in the waveguide which divides the input sampling beam S1 equally (i.e. 50/50) into two output sampling light S1beams. This occurs successively in each of the 3 rows of waveguide splitters for convenience to create the 8 output sampling beams S1 in the illustrated prototype embodiment developed. However, in other embodiments a lesser or greater number of rows including even a single splitter row (e.g. 1×8 splitter in this example) may be used to split the sampling light S1 into the desired number of sampling beams for scanning the sample. The number of rows of splitters used does not limit the invention and may be dictated in some embodiments by the geometry and/or size of the photonic chip 101 desired for the given application. It further bears noting that more or less than eight sampling beams or channels may be used in other embodiments as needed and the invention is expressly not limited to the eight beam prototype embodiment.

Each of the 8 beams of sampling light S1 were then transmitted in a separate waveguide channel 103 through the chip, thereby forming a plurality of output beams or channels emitted from photonic chip 101 through a plurality of output ports 105 clustered together on one side 101c of substrate 102, as shown in FIG. 2. This figure includes a zoom-in view of output ports 105 of the chip showing eight waveguide output ports 105 forming output beam channels with a pitch p=0.25 mm (or 250 μm) spacing between them. Optical delays between each of the 8 waveguide channels 103 were created in the photonic chip 101 by setting different terminal path or channel lengths for each channel between the third row photonic splitters 107 and output ports 105, with a physical length (optical delay) difference ΔL in this non-limiting embodiment of about 2.5 mm in the waveguide or about 3.7 mm optical delay in air between adjacent channels, in order to generate multiplexed interference signals. The time or optical delay was created by varying the lengths of each waveguide channel 103 between the third row of the waveguide splitters 107 and the output ports 105 as shown. In a preferred embodiment, the difference ΔL is selected to produce an optical delay shorter than the coherence length of the light source between the plurality of sampling beams so that when images are formed, signals from different physical locations are detected in different frequency bands.

In one embodiment, a uniform or equal difference in length ΔL between each adjacent waveguide channel 103 may be provided for transmitting sampling light of all wavelengths in different bands. However, the delay does not need to be uniform. For some applications, as an example, the system designer may intentionally use non-uniform delays to accommodate the specific sample geometry to be scanned for example where the sample has a non-uniform and/or non-planar surface geometry in order to optimize the scanned images returned from the sample. The invention is therefore not limited to a uniform difference in length ΔL between each adjacent waveguide channel 103.

The outputs ports 105 of the waveguide photonic chip 101 were 8-degree angle polished to reduce back reflections. The overall size of the integrated photonic chip was about 2.5×2.0 cm², close to the size of a U.S. quarter coin (see, e.g. photo image of FIG. 3).

In the prototype arrangement of photonic chip 101 shown in FIG. 2, the three-row cascading splitters are arranged to split and guide the sampling light S1 beam in a first direction (downward in this figure). The terminal portions of the waveguide channels 103 associated with each output port in the time delay region of the chip, which have different predetermined lengths to create an optical time delay between each of the plurality of sampling beams or channels, are arranged generally perpendicularly to the waveguide channels 103 in the foregoing splitter region. Thus at least in the prototype chip, the incident sampling light S1 following the waveguide channel path in the time delay region travels and progresses generally perpendicularly to the sampling light path in the splitter region which advantageously conserves space on the chip 101 to minimize its size, thereby allowing creation of an extremely small photonic splitter and time delay unit. The term "generally" is used to connote that the sampling light S1 in the splitter region does not necessarily travel perfectly perpendicular to the sampling light in the time delay region when propagating through the curved and angled portions of the individual photonic splitters 107, but rather the general flow of the sampling light through these regions is perpendicular to each other in this non-limiting embodiment. In other embodiments, the flow of sampling light may be obliquely angled or parallel relative to each other in the splitter and time delay regions. Accordingly, the invention is not limited to the flow of sampling light through chip 101 illustrated in the embodiment of FIG. 2.

It will be appreciated that in other embodiments besides the foregoing prototype, different numbers of waveguide channels, length or delay differences between channels, output spacing, polish angles, chip dimensions, and configurations of waveguides may be used. Accordingly, the invention is expressly not limited to the above design and recited values of these parameters in the prototype demonstration system. Other embodiments may therefore be different in these aspects and is not limiting of the invention.

The rest of the prototype chip-based SDM-OCT system 100 components are described as follows with additional reference to FIG. 1. The light source 110 may be a commercially-available wavelength-tunable, long coherence light source to provide optimal imaging depth range. In one embodiment, without limitation, the coherence length may be greater than 5 mm to achieve proper imaging range for the SDM-OCT system. The long coherence light source 110 used in the prototype system was a VCSEL (vertical-cavity surface-emitting laser) wavelength-tunable laser diode (e.g. SL1310V1, Thorlabs Inc., USA, coherence length >50 mm). In other embodiments, other coherence lengths greater than 5 mm may be used. A booster optical amplifier (BOA) 111 (e.g. BOA 1130s, Thorlabs Inc., USA) was employed in the optical path right after the commercial VCSEL wavelength-tunable laser light source (e.g. SL1310V1, Thorlabs Inc., USA) to boost the laser output from about 27 mW to about 100 mW. The long-coherence light source 110 was optically coupled to the BOA 111 via an optical fiber 104. It bears noting that optical fibers 104 may be used to optically couple the remaining optical components and devices of SDM-OCT system 100 together as shown in FIG. 1 unless described otherwise below. Commercially available optical fibers such as Corning® SMF-28® Ultra optical fibers or others may be used to optically interconnect the devices.

The amplified light emitted from the BOA 111 was passed through a 95/5 optical coupler 120, with 5% of the light delivered to a custom Mach-Zender interferometer (MZI) 112 with an about 38.7 mm optical delay in air for phase calibration and remaining 95% of the light used for OCT imaging. The MZI light beam was first transmitted through a 50/50 optical coupler 121 upstream of the MZI 112 as shown. Both outputs from coupler 121 are directed into the MZI which produces an interference signal.

The 95% of light emitted from optical coupler 120 for OCT imaging was further divided by a 90/10 optical coupler 130, with 10% of the power sent to the reference arm R and 90% of the power used in the sample arm S. Suitable optical couplers include optical fiber couplers available from AC Photonics, Inc., Thorlabs, Inc. or other suppliers.

The incident reference arm R light beam from coupler 130 passes through circulator 150 and a polarization controller 151 (e.g. fiber polarization controllers FPC commercially available from Thorlabs, Inc. USA and others). Polarization control is useful to match polarization state of the sample and reference arms S, R in order to optimize interference signals and achieve best image quality. The reference light beam is then transmitted through collimator 152 and lens 153 which focuses the reference light beam onto reference mirror 160. The reference arm R is a non-scanning reference arm of fixed optical length which does not require changing the light path length in order to create an interference signal for coupling with the reflected light signals from the sample. The reference light reflected from mirror 160 passes back through the foregoing reference arm R components to circulator 150 for creating the interference signal.

The incident sampling light S1 beam from coupler 130 was coupled into the integrated photonic chip on sample arm S through a circulator 140 (e.g. AC Photonics, Inc.) and a polarization controller 154. The 8-beam sampling light S1 output from the chip (see, e.g. FIG. 2) via output ports 105 directly through air was captured and collimated by collimator 170 for focusing on multiple different spots or sampling locations across the surface of the sample 191. A telescope setup with a first 30 mm lens 171 and a second 50 mm lens 172 was used to expand the size of the sampling beams. A large scan lens 190 (e.g. LSM05 objective lens, Thorlabs Inc., USA) was mounted in the sample arm S after a scanning device such as a galvanometer having an oscillating XY galvanometer mirror 173 to achieve wide-field volumetric imaging of the sample 191 with SDM-OCT. The scan lens 190 had an effective focal length of 110 mm and a working distance of 93.8 mm, resulting in about 1.7 mm spacing between the adjacent beams at the focal plane and a transverse resolution of about 20 am as measured with a USAF target (see, e.g. FIG. 5, group 4, element 5). Incident power on the sample was about 3 mW for each beam. Laterally and spatially separated portions of the sample 191 are irradiated with the sampling beams to capture digital images of the sample.

It bears noting that the sample 191 can be scanned simultaneously by sampling light S1 emitted by each of the eight output ports 105 from photonic chip 101 using galvanometer mirror 173. The galvanometer includes a galvo motor with an angled vibrating/oscillating (e.g. up and down) mirror 173 driven by a motor shaft. Sampling light beams from each scanning output port 105 are independently transmitted and scanned across a surface of the sample 191 by galvanometer scanner mirror 173, thereby producing discrete and independent illuminated sampling spots or locations each corresponding to one of the output ports. The galvanometer mirror 173 may project the sampling beams S1 onto the sample in any suitable pattern to capture the desired image information. Other variations and types of scanning devices may be used. In some non-limiting examples, the galvanometer scanner 200 may be Cambridge Technologies, Model 6215H or Thorlabs, GVS102.

Reflected sample light signals S2 returned simultaneously from each sampling location on sample 191 and reference light R1 from reference arm R from mirror 160 were routed to a 50/50 optical coupler 141 via upstream optical circulators 140 and 150 previously described herein. During this process, reflected sample light signals travel back through the sample arm lenses 190, 171, and 172, collimator 170, and into photonic chip 101. The plurality of reflected light signals S2 are captured by the output ports 105 and then transmitted through the plurality of waveguide channels 103 in the time delay and splitter region in a reverse path and direction to the path and direction of sampling light signals S1. The multiple reflected light signals are combined into a singular reflected light signal S2 which leaves the photonic chip 101 through the sample light input port 106 and is directed to optical coupler 141. It bears noting the reflected light signal comprises a plurality of reflected light signals containing the scanned image information in different bands. Coupler 141 operates to produce a combined reflected light interference signal comprising a plurality of interference signals based on the plurality of reflected light signals S2 and reference light R1.

The reflected interference signals from both the OCT via coupler 141 and interference signal generated by MZI 112 were detected by dual balanced detectors 180 and 181 (e.g. PDB480C-AC, 1.6 GHz, Thorlabs Inc.) and their outputs were acquired simultaneously by a dual-channel high-speed data acquisition card 183 (e.g. ATS 9373, Alazar Technologies Inc.) operating at a sampling rate of 1.5 GS/s. The sampling rate was estimated by calculating the fringe frequency based on information such as the sweep rate and tuning range of the laser, and total imaging depth needed by 8 parallel imaging channels. The sampling rate was kept at least twice of the maximum fringe frequency to fulfill the Nyquist sampling requirement. Total imaging depth measured was ~31.6 mm in air or ~23.8 mm in tissue, which was sufficient to cover the OCT signals from all the 8 beams separated with different optical delays. The detected signal is digitized by the high speed data acquisition card 183 and streamed to an appropriately configured computer 184 to generate OCT scan images of the sample 191 captured by SDM-OCT system 100.

The acquired signal data from data acquisition card 183 is streamed continuously to the memory of computer 184 or memory accessible to another suitable processor-based device or PLC (programmable logic controller) through a suitably configured port. The signal data may be stored on the memory for further processing, display, export, etc.

The "computer" 184 as described herein is representative of any appropriate computer or server device with central processing unit (CPU), microprocessor, micro-controller, or computational data processing device or circuit configured for executing computer program instructions (e.g. code) and processing the acquired signal data from data acquisition card 183. This may include, for example without limitation, desktop computers, personal computers, laptops, notebooks, tablets, and other processor-based devices having suitable processing power and speed. Computer 184 may include all the usual appurtenances associated with such a device, including without limitation the properly programmed processor, a memory device(s), a power supply, a video card, visual display device or screen (e.g. graphical user interface), firmware, software, user input devices (e.g., a keyboard, mouse, touch screen, etc.), wired and/or wireless output devices, wired and/or wireless communication devices (e.g. Ethernet, Wi-Fi, Bluetooth, etc.) for transmitting captured sampling images. Accordingly, the invention is not limited by any particular type of processor-based device.

The memory may be any suitable non-transitory computer readable medium such as, without limitation, any suitable volatile or non-volatile memory including random access memory (RAM) and various types thereof, read-only memory (ROM) and various types thereof, USB flash memory, and magnetic or optical data storage devices (e.g. internal/external hard disks, floppy discs, magnetic tape CD-ROM, DVD-ROM, optical disk, ZIP™ drive, Blu-ray disk, and others), which may be written to and/or read by a processor operably connected to the medium.

Figure 4:
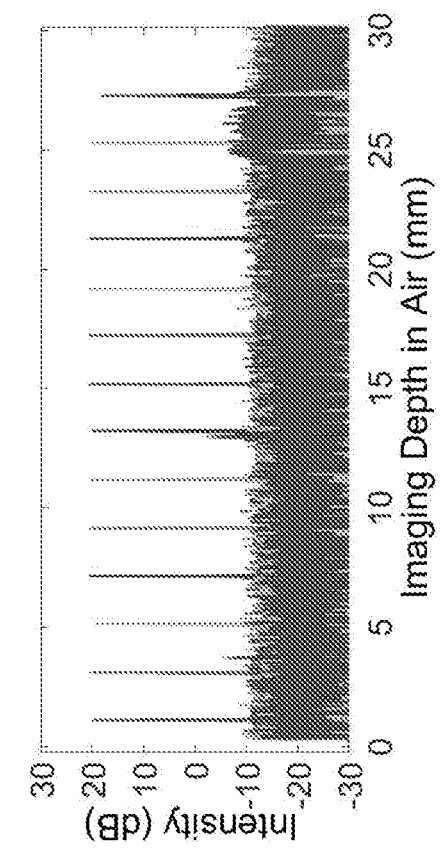
FIG. 4 is a diagram or chart showing roll-off measurement of the central beam of the chip-based SDM-OCT in logarithmic scale.

It will further be appreciated that various aspects of the present embodiment may be implemented in software, hardware, firmware, or combinations thereof. The computer programs described herein are not limited to any particular embodiment, and may be implemented in an operating system, application program, foreground or background process, driver, or any combination thereof, executing on a single computer or server processor or multiple computer or server processors The result of a sensitivity roll-off measurement for the central beam of the SDM-OCT system 100 is shown in FIG. 4. The sensitivity of the chip-based SDM-OCT was measured as about 91 dB with a calibrated −47.2 dB reflector as the sample. A roll-off of about 2 dB was observed over about 27 mm depth range. The axial resolution was maintained as about 11 am in air or about 8.3 µm in tissue throughout the entire imaging depth. The performance of the SDM-OCT system 100 with photonic chip 101 was similar to good results achieved with earlier non-chip SDM-OCT prototype systems similar to that disclosed in FIG. 1 of U.S. Pat. No. 9,400,169.

Advantageously, the present SDM-OCT system 100 realized an eight times increase in imaging speed, reaching about 800,000 A-scans/s, was achieved with the chip-based SDM-OCT system as compared to a single-spot SS-OCT with the same VCSEL running at 100 kHz. A sensitivity of about 91 dB was measured with the chip-based SDM-OCT. The feasibility of high-speed chip-based SDM-OCT was demonstrated with wide-field imaging capabilities. Three-dimensional (3D) volumetric images (700×1200 A-scans) of ex vivo porcine eye and in vivo human finger print covering a large imaging area of up to 18.0×14.3 mm² was obtained in about 1 second. High-definition 3D OCT images (1500× 1600 A-scans) of human finger nail were acquired in about 3 seconds. Integrated photonic devices can be reliably manufactured with high precisions and low per-unit cost, facilitating the deployment and adoption of the SDM-OCT technology.

During the testing, two scanning protocols were employed for wide-field OCT volumetric imaging using SDM-OCT system 100: (1) Fast-scanning mode: OCT volumetric data, consisting a total number of 700×1200 A-scans for all eight beams (700×150 A-scans was acquired for each beam), was obtained in about 1 second. This helps minimize motion artifacts, especially for in vivo imaging. (2) High-definition mode: OCT volumetric data, which consisted of 1500×1600 A-scans for all eight beams (1500×200 A-scans was acquired for each beam) was obtained in 3 seconds in order to achieve Nyquest sampled transverse resolution and preserve details of the sample. The size of each OCT volumetric data was about 3.3 GB in fast-scanning mode and ~9.3 GB in high-definition mode. During the scanning, each beam was moved up to about 18 mm in the fast scanning axis direction, and about 2.4 mm in the slow axis direction. Wide-field OCT data was obtained by stitching 3D OCT images from all 8 beams.

With respect to the foregoing optical couplers or splitters described (e.g. 120, 130, etc.), it will be appreciated that any suitable optical division or splitting of input light beams identified as a percentage of the incident beam (e.g. 5/95, 10/90, etc.) may be used depending on the intended application and system parameters. Accordingly, the invention is expressly not limited to those light division or split percentages disclosed herein which represent merely some of many possible designs that might be used for the couplers. It will be appreciated by those skilled in the art that the determination of the optical split ratio depends on how much light is intended to be directed into each of the sample and reference arms. It is desirable to have as much power as possible on sample while keep the power on sample to be within a safe limit. In the meantime, sufficient power is needed on the reference arm to get shot-noise limited sensitivity.

Figure 5:
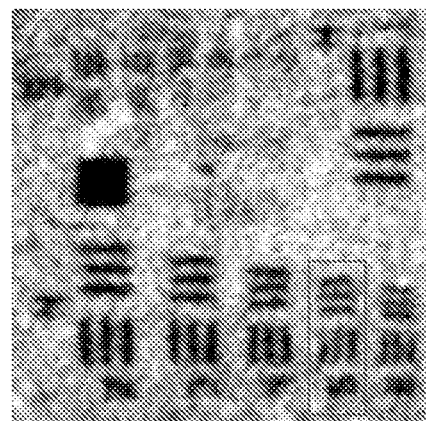
FIG. 5 is a 1951 USAF resolution test target image showing transverse resolution of the chip-based SDM-OCT prototype system.

FIG. 5 is a 1951 USAF resolution test target image showing transverse resolution of the first prototype chip-based SDM-OCT system. The USAF target is widely accepted to test the resolution of optical imaging systems such as microscopes, cameras and image scanners. Transverse resolution of the first prototype chip-based SDM-OCT system was measured to be about 20 am with a USAF target (Group 4, element 5 is clearly visible). Note that the transverse resolution of the SDM-OCT system depends on the numerical aperture of the objective lens and can be increased or decreased to fit the needs of different applications.

A method for processing light in a space division multiplexing optical coherence tomography system using integrated photonic chip 101 will be briefly presented. In one embodiment, the method comprises: providing a photonic chip comprising an optical input port, a plurality of optical output ports, and a multiple branched waveguide structure optically coupling the input port to each of the output ports, the waveguide structure comprising a plurality of interconnected waveguide channels formed in the chip; receiving a singular sample beam from a light source at the input port; dividing the sample beam into a plurality of sampling beams using a plurality of in-chip photonic splitters defined by the waveguide channels in the splitter region; creating a time delay between the plurality of sampling beams by varying a length of each waveguide channel after dividing the sampling beam; and emitting the plurality of sampling beams simultaneously in parallel through the output ports towards a sample to be scanned.

The method may further include steps of: receiving a plurality of reflected light signals returned from the sample at the output ports; transmitting the reflected light signals through the time delay region to the splitter region of the photonic chip; combining the reflected light signals into a singular reflected light signal; and emitting the singular reflected light signal from the input port of the photonic chip. The method may further comprise steps of: creating an interference signal by combining the reflect light signal with a reference light signal; producing digital images of the sample using a digitizer based on the interference signal. In one embodiment, the plurality of sampling beams are transmitted through waveguide channels in the time delay region of different lengths to create the time delay between the plurality of sampling beams.

Low Insertion Loss SDM-OCT System and Photonic Chip

Typically, when light is split from 1 fiber to N output channels using a photonic chip 101 as described above, the intensity for each of the output fiber is about 1/N of the input intensity. This allows even distribution of the light through all the output channels of the photonic chip for sampling. When reflected light is collected and returned from the sample passing back through the chip 101 again in the reverse direction, only about 1/N of the returned light is combined in the input fiber 104 to the chip leading the reflected light back to circulator 140. This insertion loss is proportional to how many channels the photonic chip 101 splits the light. In order to minimize the insertion loss for the returned beam, an alternative embodiment of a photonic chip-based SDM-OCT system 200 with chip 201 is presented in FIGS. 6 and 7.

SDM-OCT system 200 seeks to reduce return optical losses and coupling losses at the input/output of the photonic chip 201. This design allows light to be split only on the first pass through the photonic chip 101 to the sample 191. Back-reflected light returned from the sample avoids the on-chip optical splitters and the input port 106 and associated input fiber 104 with this chip topology resulting in much lower losses. Unlike the photonic chip 101 of FIGS. 1-3 described above, reflected light signals returned from the sample 191 during the sampling process which produces the digitized images of the sample do not pass through the input fiber 104 of the present low loss photonic chip 201. The key design aspect in photonic chip 201, however, is that the returned reflected light signals S2 will only pass through one row of couplers or splitters 230 shown in the rectangular box in FIG. 7 indicating "sample splitters". The signal will be routed to interfere with reference light. This way, the top two rows of couplers or splitters 230 (each row produces 3 dB loss) from the input will be by-passed to avoid 6 dB light loss. Therefore, it bears noting that bypassing the input port 206 and fiber 204 is a consequence of this bypass design implementation and is not in itself the key factor.

Figure 7:
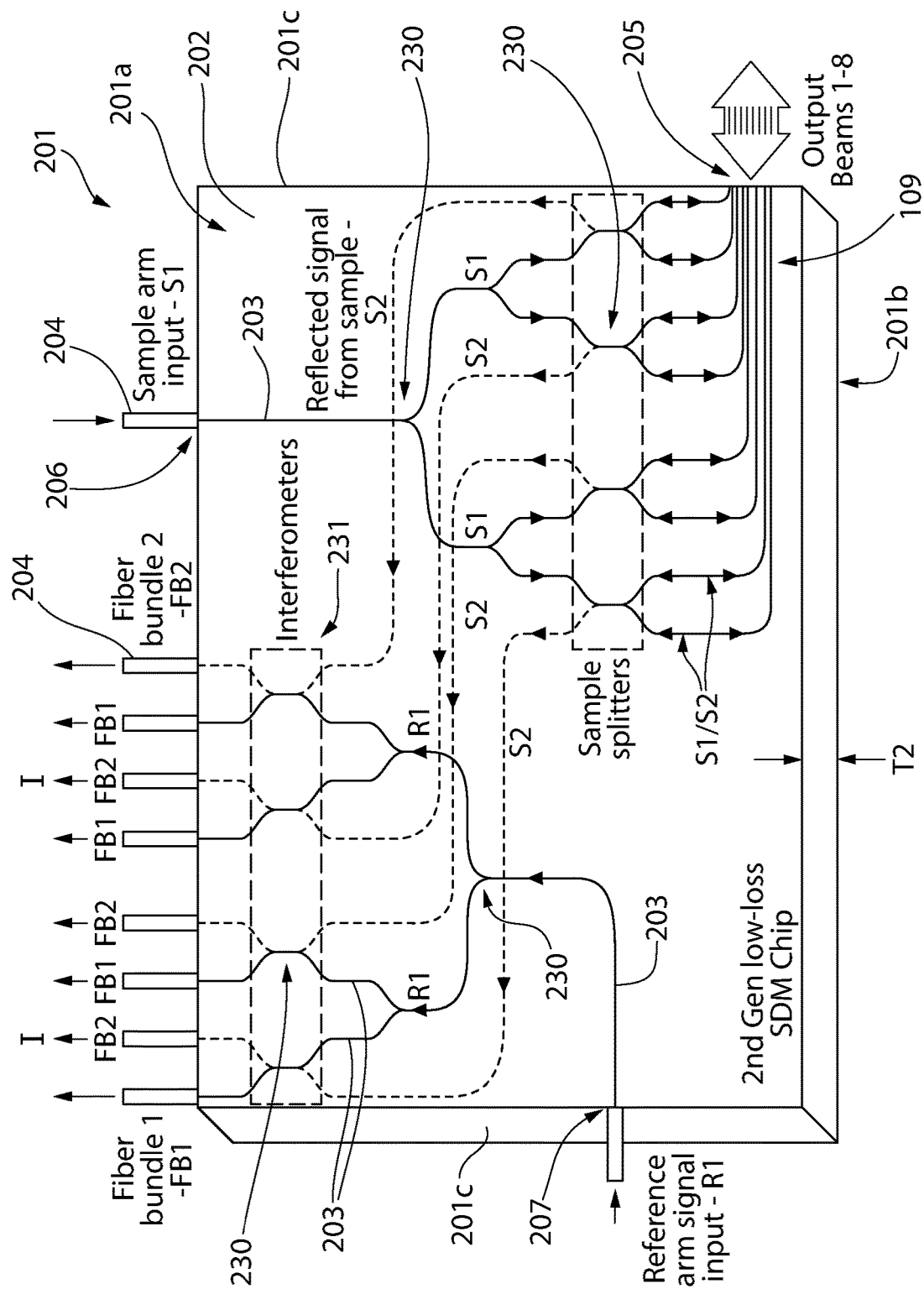
FIG. 7 is a schematic diagram of the photonic chip of FIG. 6 showing an exemplary waveguide architecture.

Referring to FIG. 7, the low loss photonic chip 201 comprises a substrate 202 which may have a generally rectangular prismatic or cuboid configuration in one embodiment comprising a parallel major surfaces 201a, 202b defining a thickness T2 therebetween, and a four perpendicular side surfaces 201c defining a perimeter of the chip. Substrate 202 is formed of a material having a first refractive index Ri1. In the prototype system, the substrate 202 may have a thickness T2 of about 1-2 mm. Other thicknesses, however, may be used for substrate 202. The substrate 202 may be made of any of the same materials suitable material for constructing a photonic chip as substrate 102 described above. In one example without limitation, the substrate may be formed of silicon.

Low loss photonic chip 201 has a plurality of different input and output ports for receiving and transmitting light signals to and from the chip which travel or propagate through waveguide channels therein. In one embodiment, chip 201 may have a sample beam input port 206 which receives an input sample light signal from the sample arm S sample beam input optical fiber 204 generated by light source 110, a plurality of output ports 205 which transmit sampling beams S1 to the sample 291 and receive reflected light signals S2 returned from the sample, a reference signal input port 207 receiving a reference signal R1 from the reference arm R, and a plurality of interference signal output ports 208 for transmitting interference signals to digital balanced detector 280. Outputs ports 205 of the waveguide photonic chip 101 may be 8-degree angle polished to reduce back reflections. Other polishing angles may be used control the amount of surface reflection.

Similarly to photonic chip 101, a multiple branched waveguide structure comprising a plurality of waveguide channels 203 are formed in low loss chip 201 and may lie in the same horizontal reference plane. Photonic chip 201 is patterned with an array or plurality of waveguide channels 203 configured to form a splitter region, time delay region, and interferometer region. Similarly to chip 101, the difference in the refractive indices at the interface of the waveguide channels 203 and base substrate 202 confine and cause the light signal to travel within the waveguide channels 203 with minimal or no scattering of light into the adjoining base portions of the substrate.

Referring to FIG. 7, the waveguide channels 203 may have the same cross-sectional geometry in some constructions. In one embodiment, the waveguide channels 203 may be optimized for 1060 nm light operation. Ophthalmic swept-source OCT systems typically operate at 1060 nm center wavelength to avoid the high absorption of water at the 1310 nm bandwidth. The cross sectional geometry of the waveguide channels 203 must therefore be redesigned to ensure efficient propagation of light signals at the target wavelength. The waveguide channels may be designed for other center wavelengths in other embodiments depending on the intended scanning application and requirements.

The waveguide channels 203 are patterned to form a three-row sample splitter region similarly to chip 101 to split the incident single sampling beam into eight output sampling beams or channels in the non-limiting illustrated chip example. Other numbers of output sampling beams may be used in other embodiments. The final or third row sample splitters location is denoted in FIG. 7 by the first labelled dashed box shown (the 1st and 2nd splitter rows are shown above the dashed box). A distinct interferometer region is patterned on the chip 201 denoted by the second labelled dashed box which receives 4 reference light signals R1 each of which interferes with a reflected light signal S2 received from the sampling splitter region which collects the reflected light returned from the sample 291. The incident single reference light signal R1 is divided into the four reference light signals R1 by patterning the reflected light waveguide channels 203 with the appropriate number of branches as shown. In one embodiment, all the reference light R1 waveguide channels may have the same optical path length whereas the sample arm sampling light S1 waveguide channels have different optical path lengths to produce the optical time delay.

In another embodiment, however, all the sampling light S1 waveguide channels 203 may have the same optical path length while the reference light R1 waveguide channels 203 instead have different optical path lengths analogous to the above mentioned optical delays between channels. In fact, a combination of sample arm and reference arm waveguide layout design may be used to generate the same differential optical path length delay between different interference signals originated from different imaging channels. The optical path length difference is used to shift the frequency of the interference signal from different imaging channels into different frequency bands, which correspond to different depth ranges in the acquired OCT image. Accordingly, the invention is not limited to necessarily having the same optical path lengths for either the sample arm S or reference arm R. The interference signals from different channels are formed into different frequency bands when the optical path length difference between individual sample arms and reference arms is unique. Since all the interference signals are in different frequency bands, a single photodetector may be used to detect all the signals at once simultaneously in parallel.

Figure 6:
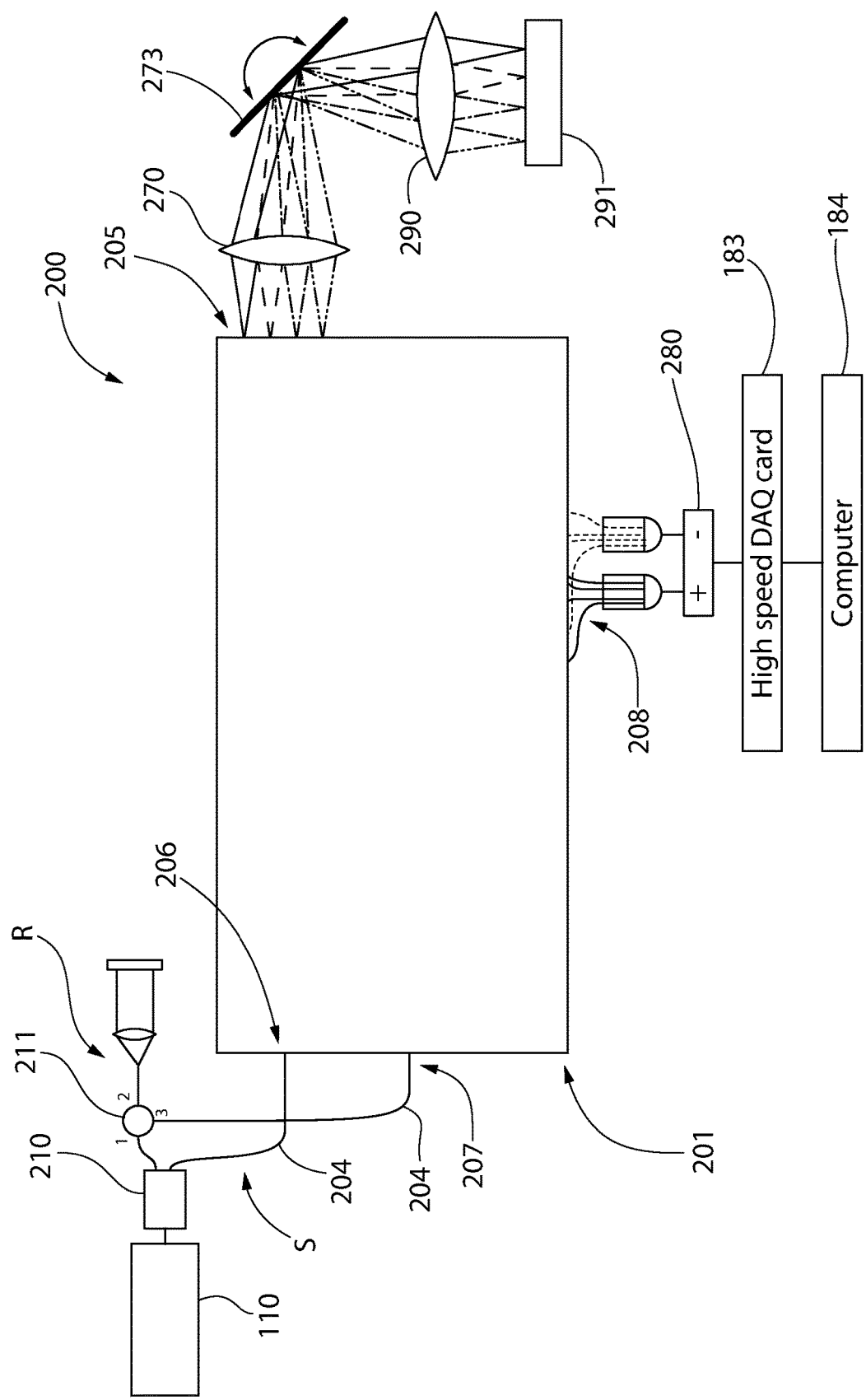
FIG. 6 is a schematic diagram of a space-division multiplexing optical coherence tomography (SDM-OCT) system incorporating a low insertion loss photonic chip according to another embodiment of the present disclosure.

FIG. 6 shows the SDM-OCT system 200 with the integrated low loss photonic chip 201. Referring to FIGS. 6 and 7, optical coupling of external devices of system 200 to the various waveguide channel ports of the photonic chip 201 may be made with optical fibers 204 in order to connect to the rest of the SDM OCT system components shown. Light is transmitted from the long coherence swept source light source 110 previously described herein through optical fiber 204 to a 20/80 optical coupler 210. Light source 110 in this embodiment may be a 200 kHz swept source laser to maximize the effective A scan rate while allowing sufficient dwell time for acceptable sensitivity. The coupler 210 directs 20% of the light directed via an optical fiber to one of the three ports in circulator 211 in the reference arm R. The remaining 80% of light emitted from coupler 210 is directed via an optical fiber to the sampling arm S and photonic chip 201 to provide the sampling light S1. Other splits for coupler 210 may be used in other embodiments as appropriate. The sampling light S1 is received at input port 206 of the chip.

The incident single beam sampling light S1 travels through the 3-row cascade of photonic waveguide splitters 230 in chip 201 formed by waveguide channels 203 which equally and gradually divide the incident light in each row into the final eight output sampling beams S1. Each photonic waveguide splitter 230 is formed by a branch in the waveguide which divides the input sampling beam S1 equally (i.e. 50/50) into two output sampling beams S1. This occurs in each of the three rows of waveguide splitters to gradually create 8 output sampling beams in the illustrated embodiment. Different splitter arrangements and/or number of rows may be used in other embodiments as previously described herein. A time delay is produced between each of the sampling light S1 beams between the splitters 230 and output ports 205 in which the difference ΔL in the predetermined lengths between the waveguide channels is selected to produce an optical delay shorter than a coherence length of the light source between the plurality of sampling beams so that when images are formed, signals from different physical locations are detected in different frequency bands. The 8-beam sampling light S1 output from the chip 201 is then collimated by collimator 270 for focusing on multiple discrete spots or sampling locations across the surface of the sample 291. The plurality of sampling beams S1 are transmitted to oscillating XY galvanometer mirror 173 to achieve wide-field volumetric imaging of the sample 191 with SDM-OCT. A large scan lens 290 (objective lens) receives and irradiates the sample 291 with the sampling beams S.

Reflected light signals S2 returned from sample 291 are captured by photonic chip 201. Reflected sample light signals S2 travel back through the sample arm scan lens 290 and collimator 170 and are received by the output ports 205 on photonic chip 101. Light signals S2 each travel through one of the eight discrete waveguide channels 203 back to the last third row of waveguide splitters 230. In the present embodiment, the waveguide splitters 230 in the final third horizontal row are configured with two inlets and two outlets instead of one inlet and two outlets like the splitters 230 shown in the first and second rows of the splitter region. A first inlet of splitters 230 in the third row receives sampling light S1 and splits the light into two sampling light beams S1 transmitted through the two first and second outlets. The second inlet forms a reflected sample light S2 output which directs the reflected light signals returned from sample 291 to the interferometer unit or region of photonic chip 201, which in turn comprises a plurality of waveguide photonic interferometers 231 formed by waveguide couplers or splitters 230 also having four branches. Each third row waveguide splitter 230 combines two of the eight reflected light signals S2 to form four reflected light signals as shown.

Each waveguide photonic interferometer 231 receives one of four reflected sample light S2 signals transmitted by the foregoing third row waveguide splitters 230 and one of four corresponding reference light signals R1 formed by waveguide splitters 230 which divide the single the reference light signal received from the reference arm R by the photonic chip 201 into four via a two row cascade of splitters.

Reflected light signals S2 returned from sample 291 and reference light R1 from reference arm R are combined to create a plurality of interference signals I. The interference signal I generated by each waveguide photonic interferometer 231 are split into two interference signals I as shown which are transmitted to the interference signal output ports 208 on chip 201. The output ports 208 are grouped into two fiber bundles FB1 and FB2 each comprising a plurality of optical fiber 204; one fiber coupled to each one of the output ports 208. The fibers 204 transmits interference signals I to a single balanced detector 280. The output signal from detector 280 is acquired by a dual-channel high-speed data acquisition card 183. The detected signal will be digitized with the high speed data acquisition card 183 and streamed to computer 184 to generate OCT scan images of the sample captured by SDM-OCT system 200.

In the foregoing scheme, the desired optical delay between each sampling light S1 can be adjusted by varying the length of each waveguide channel 203 as needed in the time delay region 109 of the photonic chip 201 to create a delay between each channel in the same manner previously described herein. The temporal delay is a function of the optical path length of each of the channels. In this embodiment, one skilled in the art can optimize the optical or time delay for use with a 200 kHz swept source laser to maximize the effective A scan rate while allowing sufficient dwell time for acceptable sensitivity. The spacing between the output sampling light S1 beams can also be independently adjusted to project the beams on the sample with a specific physical separation on the surface of the sample between imaging regions.

The waveguide channels 203 and structures such as the cascading sample beam splitters and interferometers shown in FIG. 7 may be formed in the same horizontal plane on photonic chip 201 in one embodiment. Although some portions of the waveguide channels 203 intersect or cross each other as shown, cross-talk between the waveguides at the intersections will be very small (−40 dB) with proper design in accordance with methods known in the art (see, e.g. Y. Ma et al., "Ultralow loss single layer submicron silicon waveguide crossing for SOI optical interconnect," Optics Express 21(24), 29374-29382 (2013)). In other embodiments, the waveguide channel optical structures in photonic chip 201 may be arranged in a three dimensional manner such that different optical structures may be found in two or three vertical layers or levels within the chip using semiconductor fabrication techniques known in the art and used for building multi-level circuits. Such a chip architecture could completely or substantially avoid crosses or intersections between the waveguides to virtually eliminate cross talk and provide even better performance.

Figure 8:
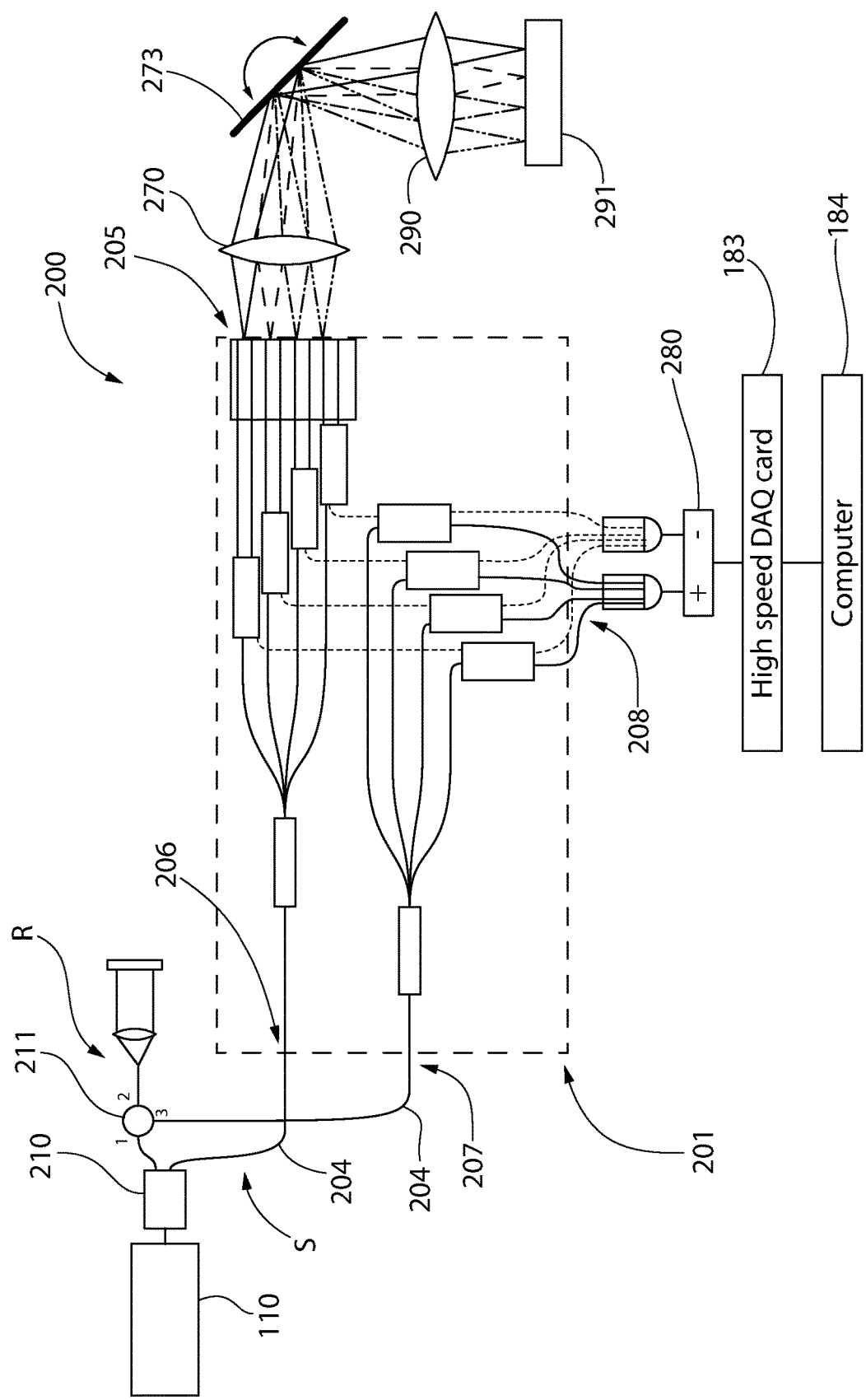
FIG. 8 is the schematic diagram of FIG. 6 showing the standard non-chip optical components and devices of the system which can be replaced by the on-chip waveguide photonic devices created by the photonic chip.

FIG. 8 illustrates how all of the traditional optical coupler/splitter devices can advantageously be replaced by the single low loss photonic chip 201 with the foregoing on-chip patterned photonic components and waveguide structures shown in FIG. 7. All of the traditional optical devices shown within the dashed box are replaced by the photonic chip 201.

Figure 9:
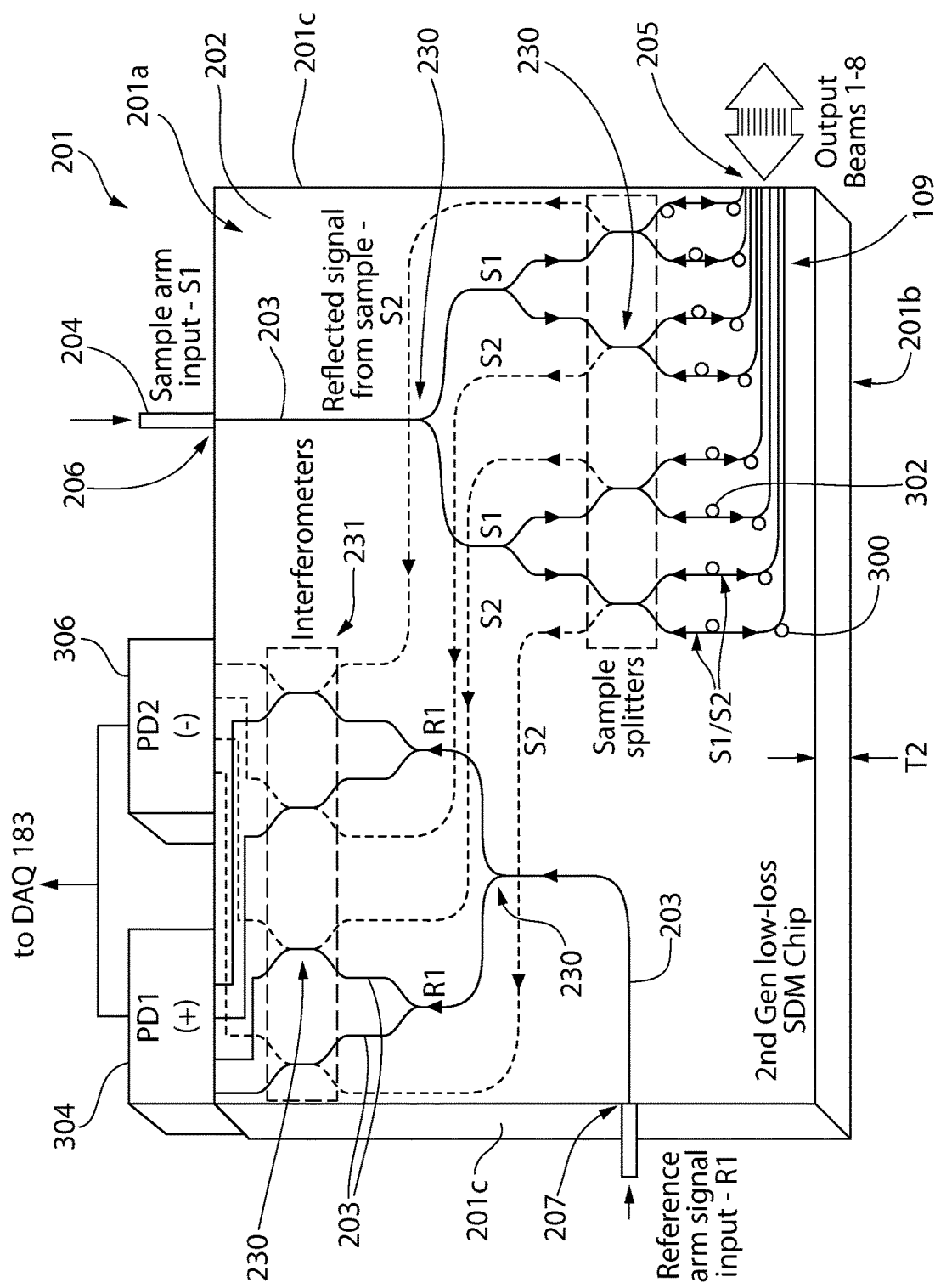
FIG. 9 is a schematic diagram of a first alternative embodiment of the chip of FIG. 7 with directly attached on-chip photodetectors.

FIG. 9 illustrates another embodiment of the low loss photonic chip 201. The layout of the chip is similar to FIG. 7, except that output fibers (FB1s and FB2s) are completely eliminated. Instead, outputs from the interferometers 231 are grouped and coupled directly into the + and − photodetectors 304, 306 (PD+ and PD−) used for the balanced detector 280. The PD+ and PD− may be directly attached such as epoxied on the side of the photonic chip to integrate the photonic chip with the detection electronics. The advantage of this embodiment is that the coupling and transmission loss of the fiber bundles are eliminated.

Figure 10:
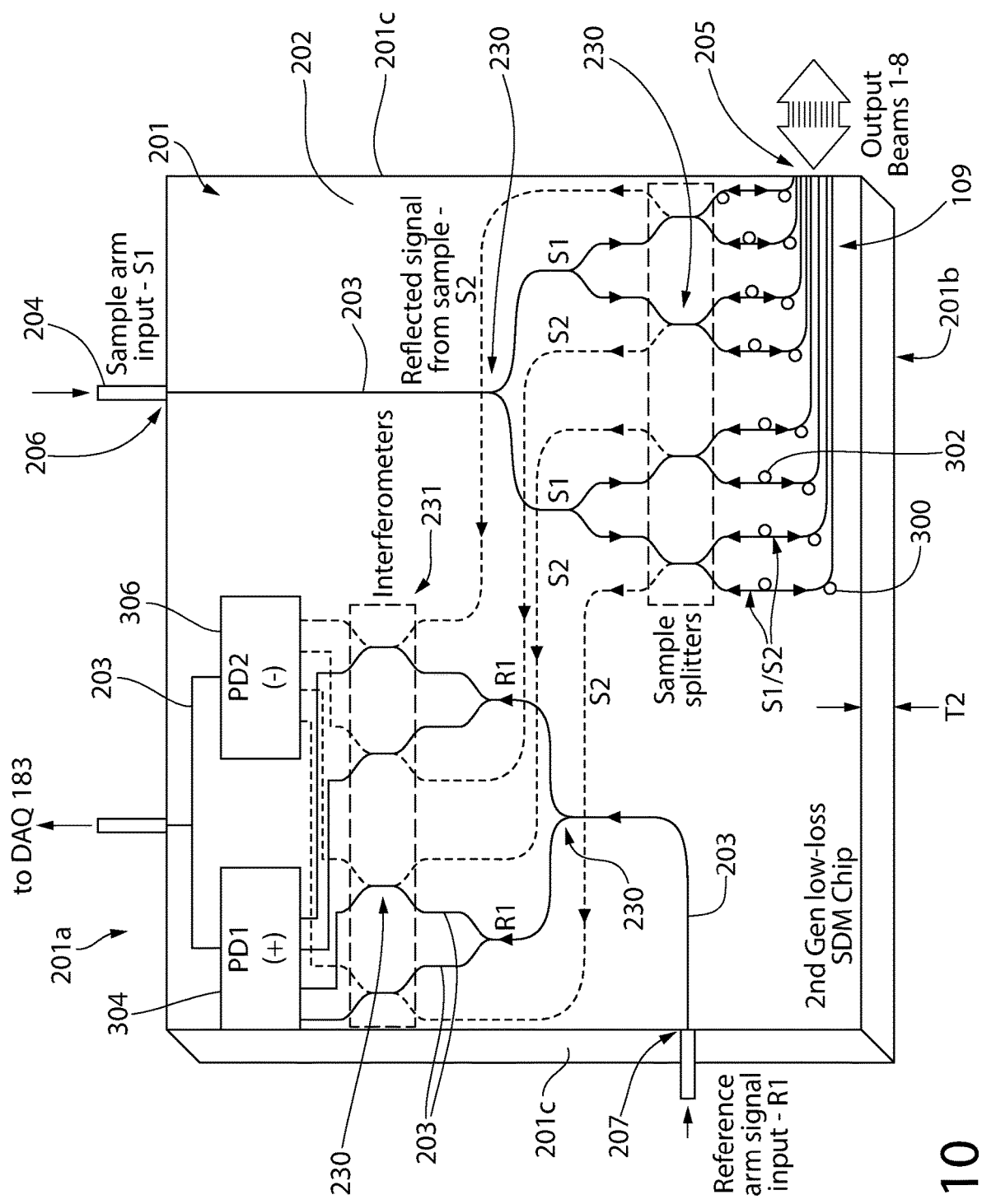
FIG. 10 is schematic diagram of a second alternative embodiment of the chip of FIG. 7 with directly embedded in-chip photodetectors formed integrally with the chip.

In addition, FIG. 10 illustrates an embodiment of the low loss photonic chip, where photodetectors 304, 306 (PD+ and PD−) and detection electronics may be directly integrated on the chip as active components. In fact, the silicon substrate is often used to develop electro-optical devices, including photodetectors, phase modulators, and polarization controllers, etc. Such techniques are described for example in A. Cutolo et al.; Silicon electro-optic modulator based on a three terminal device integrated in a low-loss single-mode SOI waveguide, Journal of Lightwave Technology, 15(3), 505-518, 1997, and other technical publications. Phase modulators 302 and polarization controllers 300 may thus be included in each of the sampling channels as shown in the embodiments of both FIGS. 9 and 10. This allows individual control of the phase and polarization states of the light incident on the sample and returned on the interferometers in order to achieve optimal OCT image quality.

A method for processing light in a space division multiplexing optical coherence tomography system using low loss integrated photonic chip 201 will now be briefly described. In one embodiment, the method comprises: providing a photonic chip comprising an optical input port, a plurality of optical output ports, and a multiple branched waveguide structure optically coupling the input port to each of the output ports, the waveguide structure comprising a plurality of interconnected waveguide channels formed in the chip; receiving a singular sample beam from a light source at the input port; dividing the sample beam into a plurality of sampling beams using a plurality of in-chip photonic splitters defined by the waveguide channels in the splitter region; creating a time delay between the plurality of sampling beams by varying a length of each waveguide channel after dividing the sampling beam; and emitting the plurality of sampling beams simultaneously in parallel through the output ports towards a sample to be scanned; receiving a plurality of reflected light signals returned from the sample at the output ports; transmitting the reflected light signals to a plurality of interferometers defined by the waveguide channels in an interferometer region of the photonic chip; combining the reflected light signals with a reference light signal using the plurality of interferometers to generate a plurality of interference signals; and emitting the interference signals from interference output ports of the photonic chip.

It expressly bears noting that although somewhat distinct on-chip photonic beam splitter and optical time delay regions are shown in the illustrated embodiments of photonic chips 101 and 201 for simplicity of design and fabrication, the present invention does not necessarily require that the beam splitting and time delay functionality be performed in separate regions or areas of the chips. Accordingly, the beam splitting and time delay functions may be performed in a single combined or mixed splitter and time delay region or area of the chips in other embodiments contemplated in which optical light path lengths. For example, different optical path or waveguide channel lengths may be used between successive rows of splitters to create the optical delay.

It expressly bears noting that although several linear rows of in-chip photonic splitters 107, 230 are disclosed herein, other embodiments may have more random or staggered arrangements of splitters which are not linear and/or may not be aligned into rows. Accordingly, the invention is not limited to formation of cascading linear rows of splitters represented merely one of many possible configurations and arrangements of splitters that may be formed by the waveguide channels 103 and 203.

While the foregoing description and drawings represent exemplary embodiments of the present invention, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes as applicable described herein may be made without departing from the spirit of the invention. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, which may be made by those skilled in the art without departing from the scope and range of equivalents of the invention.

What is claimed is:

1. An integrated photonic chip suitable for space-division multiplexing optical coherence tomography scanning, the photonic chip comprising:
   a substrate;
   an optical input port configured to receive an incident singular sampling beam from an external light source;
   a plurality of optical output ports configured to transmit a plurality of sampling beams from the chip to a sample to capture scanned images of the sample; and
   a multiple branched waveguide structure optically coupling the input port to each of the output ports, the waveguide structure comprising a plurality of interconnected waveguide channels formed in the substrate;
   the waveguide channels configured to define a plurality of photonic splitters which divide the incident singular sampling beam received at the input port into the plurality of sampling beams at the output ports;
   wherein portions of the waveguide channels between the photonic splitters and output ports have different predetermined lengths to create an optical time delay between each of the plurality of sampling beams;

wherein a difference in the predetermined lengths between the waveguide channels is selected to produce an optical delay shorter than a coherence length of the light source between the plurality of sampling beams so that when images are formed, signals from different physical locations are detected in different frequency bands.

2. The photonic chip according to claim 1, wherein the photonic splitters are arranged in multiple cascading rows on the substrate, the singular sampling beam being successively divided in each row by the photonic splitters to create an increasingly greater number of sampling beams in each row between the inlet port and the output ports.

3. The photonic chip according to claim 1, wherein the output ports emit the sampling beams from the photonic chip directly into air to the sample.

4. The photonic chip according to claim 1, wherein the output ports are arranged to receive a plurality of reflected light signals returned from the sample, the photonic splitters being configured to combine the plurality of reflected light signals into a singular reflected light signal which is emitted from the input port of the photonic chip.

5. The photonic chip according to claim 1, wherein the plurality of output ports are clustered together on one side of the substrate and evenly spaced apart at a predetermined pitch spacing.

6. The photonic chip according to claim 5, wherein a difference in length between each adjacent waveguide channel in the photonic chip is the same.

7. The photonic chip according to claim 1, further comprising an optical fiber coupled to the input port of the photonic chip.

8. The photonic chip according to claim 1, wherein the substrate is selected from the group consisting of silicon, silicon on insulator, Iridium Phosphide, Lithium Niobate, Silicon Nitride and Gallium Arsenide.

9. The photonic chip according to claim 1, wherein the sampling beams in the time delay region travel in a path generally perpendicular to a path of the sampling beams in the splitter region.

10. The photonic chip according to claim 1, wherein the waveguide channels are etched into the substrate.

11. A low loss integrated photonic chip suitable for space-division multiplexing optical coherence tomography scanning, the photonic chip comprising:
 a substrate;
 an optical input port configured to receive an incident singular sampling beam from an external light source;
 a reference light input port configured to receive reference light from an external reference light source;
 a plurality of optical output ports configured to transmit a plurality of sampling beams from the chip to a sample to capture scanned images of the sample;
 a multiple branched waveguide structure optically coupling the input port to each of the output ports, the waveguide structure comprising a plurality of interconnected waveguide channels formed in the substrate, the waveguide channels defining a splitter region and an interferometer region;
 the waveguide channels in the splitter region configured to define a plurality of photonic splitters which divide the incident singular sampling beam received at the input port into the plurality of sampling beams at the output ports;
 wherein portions of the waveguide channels between the photonic splitters and output ports have different predetermined lengths to create an optical time delay between each of the plurality of sampling beams;
 the waveguide channels in the interferometer region configured to define a plurality of photonic interferometers, the photonic interferometers optically coupled to the waveguide channels in the time delay region and the reference light;
 wherein the photonic interferometers are arranged to receive a plurality of reflected light signals returned from the sample, the photonic interferometers being configured and operable to combine the reflected light signals with the reference light to produce a plurality of interference signals which are emitted from interference signal output ports of the photonic chip.

12. The photonic chip according to claim 11, wherein the photonic splitters are arranged in multiple cascading rows on the substrate, the singular sampling beam being evenly and successively divided in each row by the photonic splitters to create an increasingly greater number of sampling beams in each row between the inlet port and the output ports.

13. The photonic chip according to claims 12, wherein the photonic interferometers are optically coupled to photonic splitters in a final row of the splitter region.

14. The photonic chip according to claim 13, wherein the reflected light signals returned from the sample travel through the photonic splitters in the final row to the interferometers and bypass preceding rows of photonic splitters in the splitter region.

15. The photonic chip according to claim 11, wherein the photonic interferometers are optically coupled to the reference light input port via a plurality of reference light waveguide channels.

16. The photonic chip according to claim 11, wherein a difference in the predetermined lengths between the waveguide channels is selected to produce an optical delay shorter than a coherence length of the light source between the plurality of sampling beams so that when images are formed, signals from different physical locations are detected in different frequency bands.

17. A method for processing light in a space division multiplexing optical coherence tomography system using a low loss integrated photonic chip, the method comprising:
 providing a photonic chip comprising an optical input port, a plurality of optical output ports, and a multiple branched waveguide structure optically coupling the input port to each of the output ports, the waveguide structure comprising a plurality of interconnected waveguide channels formed in the chip;
 receiving a singular sample beam from a light source at the input port;
 dividing the sample beam into a plurality of sampling beams using a plurality of in-chip photonic splitters defined by the waveguide channels in the splitter region;
 creating a time delay between the plurality of sampling beams by varying a length of each waveguide channel after dividing the sampling beam; and
 emitting the plurality of sampling beams simultaneously in parallel through the output ports towards a sample to be scanned;
 receiving a plurality of reflected light signals returned from the sample at the output ports;
 transmitting the reflected light signals to a plurality of interferometers defined by the waveguide channels in an interferometer region of the photonic chip;

combining the reflected light signals with a reference light signal using the plurality of interferometers to generate a plurality of interference signals; and emitting the interference signals from interference output ports of the photonic chip.

* * * * *